US010675435B2

(12) United States Patent
Herrera et al.

(10) Patent No.: US 10,675,435 B2
(45) Date of Patent: *Jun. 9, 2020

(54) EXTENDED-USE VALVED URINARY CATHETER

(71) Applicant: Spinal Singularity Inc., San Clemente, CA (US)

(72) Inventors: Derek Herrera, San Clemente, CA (US); Alex Shen, Los Angeles, CA (US)

(73) Assignee: Spinal Singularity, Inc., San Clemente, CA (US)

(*) Notice: Subject to any disclaimer, the term of this patent is extended or adjusted under 35 U.S.C. 154(b) by 532 days.

This patent is subject to a terminal disclaimer.

(21) Appl. No.: 15/072,345

(22) Filed: Mar. 16, 2016

(65) Prior Publication Data

US 2016/0287847 A1 Oct. 6, 2016

Related U.S. Application Data

(63) Continuation-in-part of application No. PCT/US2016/014648, filed on Jan. 23, 2016.
(Continued)

(51) Int. Cl.
*A61M 25/00* (2006.01)
*A61M 27/00* (2006.01)
(Continued)

(52) U.S. Cl.
CPC ...... *A61M 25/0017* (2013.01); *A61M 27/002* (2013.01); *A61M 25/04* (2013.01); *A61M 39/24* (2013.01); *A61M 2025/0056* (2013.01)

(58) Field of Classification Search
CPC . A61B 5/6852; A61M 25/0017; A61M 25/04; A61M 27/002; A61M 39/24;
(Continued)

(56) References Cited

U.S. PATENT DOCUMENTS 3,812,841 A 5/1974 Isaacson
4,168,699 A 9/1979 Hauser
(Continued)

FOREIGN PATENT DOCUMENTS

EP 1096900 9/2005
EP 2094343 10/2017
(Continued)

OTHER PUBLICATIONS

Notice of Allowance dated Aug. 17, 2017 in U.S. Appl. No. 15/419,948.
(Continued)

*Primary Examiner* — Leslie R Deak
(74) *Attorney, Agent, or Firm* — Snell & Wilmer L.L.P.

(57) ABSTRACT

The disclosure relates generally to an extended use systems and devices for management of bladder function for people with urinary dysfunction. The system includes a catheter and a valve that can control fluid flow. The catheter can be placed inside the bladder using devices that facilitate insertion and extraction. The placement of the catheter can be done by a trained individual such as a patient, as well as a clinician, a nurse, or a caretaker. Once placed inside the bladder, the catheter can be fully-internal, meaning no portion of the catheter is visible from outside of the patient's body.

8 Claims, 7 Drawing Sheets

Related U.S. Application Data (60) Provisional application No. 62/279,485, filed on Jan. 15, 2016, provisional application No. 62/275,671, filed on Jan. 6, 2016, provisional application No. 62/231,854, filed on Jul. 16, 2015, provisional application No. 62/141,520, filed on Apr. 1, 2015.

(51) Int. Cl.
  *A61M 39/24* (2006.01)
  *A61M 25/04* (2006.01)

(58) Field of Classification Search
  CPC .. A61M 2210/1085; A61M 2210/1089; A61M 2210/1092; A61M 2210/1096; A61M 39/22; A61F 2/0022; A61F 2/04
  See application file for complete search history.

(56) References Cited

U.S. PATENT DOCUMENTS

| | | | |
|---|---|---|---|
| 4,932,938 A * | 6/1990 | Goldberg | A61F 2/0022 251/342 |
| 5,041,092 A | 8/1991 | Barwick | |
| 5,366,506 A | 11/1994 | Davis | |
| 5,380,268 A | 1/1995 | Wheeler | |
| 5,411,507 A | 5/1995 | Heckele | |
| 5,476,434 A | 12/1995 | Kalb et al. | |
| 5,628,770 A | 5/1997 | Thome et al. | |
| 5,713,877 A | 2/1998 | Davis | |
| 6,053,897 A * | 4/2000 | Sachse | A61M 25/01 128/840 |
| 6,066,088 A * | 5/2000 | Davis | A61F 2/0022 128/DIG. 25 |
| 6,132,365 A * | 10/2000 | Sigurdsson | A61F 2/0022 600/29 |
| 6,527,702 B2 | 3/2003 | Whalen | |
| 6,565,536 B1 | 5/2003 | Sohn | |
| 6,602,243 B2 * | 8/2003 | Noda | A61B 17/00 600/549 |
| 6,638,208 B1 | 10/2003 | Ananth et al. | |
| 6,835,183 B2 | 12/2004 | Lennox et al. | |
| 7,001,327 B2 | 2/2006 | Whalen | |
| 7,147,606 B1 | 12/2006 | Chang et al. | |
| 7,338,028 B2 | 3/2008 | Zimmerling et al. | |
| 7,415,308 B2 | 8/2008 | Gerber et al. | |
| 7,803,106 B2 | 9/2010 | Whalen et al. | |
| 8,801,697 B2 | 8/2014 | Yugari | |
| 8,882,652 B2 | 11/2014 | Vitzthum | |
| 9,011,314 B2 | 4/2015 | Davis et al. | |
| 9,452,278 B2 | 9/2016 | Davis et al. | |
| 9,775,698 B2 | 10/2017 | Herrera et al. | |
| 2002/0165427 A1 | 11/2002 | Yachia et al. | |
| 2003/0229263 A1 | 12/2003 | Connors et al. | |
| 2004/0019369 A1 | 1/2004 | Duncan et al. | |
| 2004/0106899 A1 | 6/2004 | McMichael et al. | |
| 2005/0216069 A1 | 9/2005 | Cohen et al. | |
| 2006/0020297 A1 | 1/2006 | Gerber | |
| 2006/0184090 A1 | 8/2006 | Davis et al. | |
| 2006/0247723 A1 | 11/2006 | Gerber et al. | |
| 2008/0269546 A1 | 10/2008 | Wilkie et al. | |
| 2008/0294069 A1 | 11/2008 | Stickler et al. | |
| 2009/0157053 A1 | 6/2009 | Davis et al. | |
| 2010/0234876 A1 | 9/2010 | Watson | |
| 2010/0312225 A1 | 12/2010 | Armistead | |
| 2011/0054404 A1 | 3/2011 | Tanabe et al. | |
| 2011/0066139 A1 * | 3/2011 | Winegar | A61M 25/0102 604/524 |
| 2012/0316584 A1 | 12/2012 | Miles | |
| 2013/0041430 A1 | 2/2013 | Wang et al. | |
| 2013/0090630 A1 | 4/2013 | Winegar | |
| 2014/0148648 A1 | 5/2014 | Tycast et al. | |
| 2014/0213979 A1 | 7/2014 | Boyco et al. | |
| 2014/0214009 A1 | 7/2014 | Reyes | |
| 2014/0371803 A1 | 12/2014 | Grill et al. | |
| 2015/0087896 A1 | 3/2015 | Wei et al. | |
| 2015/0366462 A1 | 12/2015 | Ramos et al. | |
| 2016/0000641 A1 | 1/2016 | Driscoll et al. | |
| 2017/0156838 A1 | 6/2017 | Herrera | |
| 2018/0036107 A1 | 2/2018 | Herrera | |
| 2018/0140799 A1 | 5/2018 | Herrera | |
| 2018/0153669 A1 | 6/2018 | Herrera | |
| 2018/0153670 A1 | 6/2018 | Herrera | |
| 2018/0153671 A1 | 6/2018 | Herrera | |

FOREIGN PATENT DOCUMENTS

| | | |
|---|---|---|
| EP | 3247309 | 11/2017 |
| WO | 2000002499 | 1/2000 |
| WO | 2001010358 | 2/2001 |
| WO | 2011032150 | 3/2011 |
| WO | 2016118943 | 7/2016 |
| WO | 2017172998 | 10/2017 |

OTHER PUBLICATIONS

Final Office Action dated Jul. 13, 2017 in U.S. Appl. No. 15/419,948.
Office Action dated Jun. 16, 2017 in U.S. Appl. No. 15/419,948.
Restriction Requirement dated Mar. 23, 2017 in U.S. Appl. No. 15/419,948.
Restriction Requirement dated Jul. 5, 2018 in U.S. Appl. No. 15/072,345.
PCT; International Search Report dated Jul. 25, 2016 in International Application No. PCT/US2016/014648.
PCT; International Search Report dated Aug. 17, 2017 in International Application No. PCT/US2017/024862.
PCT; Written Opinion dated Aug. 17, 2017 in International Application No. PCT/US2017/024862.
EPO; Supplemental Search Report and Written Opinion dated Jan. 2, 2018 in EP 16740891.3.
International Preliminary Report on Patentability dated Jul. 25, 2017 in PCT/US2016/014648.
Mexico; Non-Final Office Action dated Jan. 26, 2018 in MX2017-009517.
PCT; Written Opinion dated Jul. 25, 2016 in International Application No. PCT/US2016/014648.
PCT; International Preliminary Report on Patentability dated Oct. 2, 2018 in International Application No. PCT/US2017/024862.
EPO; Supplementary European Search Report dated Jan. 19, 2018 in EP16740891.3.
PCT; International Search Report dated Jan. 28, 2019 in International Application No. PCT/US2018/053806.
PCT; Written Opinion dated Jan. 28, 2019 in International Application No. PCT/US2018/053806.
AUIPO; Office Action dated Jul. 22, 2019 in Australian Application No. 2016209038.
USPTO; Non-Final Office Action dated Aug. 26, 2019 in U.S. Appl. No. 15/877,228.
USPTO; Non-Final Office Action dated Sep. 12, 2019 in U.S. Appl. No. 15/785,405.
USPTO; Non-Final Office Action dated Sep. 13, 2019 in U.S. Appl. No. 15/785,403.
USPTO; Final Office Action dated Jan. 22, 2020 in the U.S. Appl. No. 15/721,096.
USPTO; Final Office Action dated Jan. 30, 2020 in the U.S. Appl. No. 15/785,403.
USPTO; Final Office Action dated Feb. 12, 2020 in the U.S. Appl. No. 15/785,405.
UK; Office Action dated Feb. 5, 2020 in UK. Application No. GB1713519.3.

* cited by examiner

EXTENDED-USE VALVED URINARY CATHETER

CROSS-REFERENCE TO RELATED APPLICATIONS

Any and all applications for which a foreign or domestic priority claim is identified in the Application Data Sheet as filed with the present application are hereby incorporated by reference under 37 CFR 157. This application claims priority to PCT Application PCT/US2016/014648; and U.S. Ser. No. 62/279,485, filed Jan. 15, 2016, and U.S. Ser. No. 62/275,671 filed Jan. 6, 2016, and U.S. Ser. No. 62/231,854 filed Jul. 16, 2015 and U.S. Ser. No. 62/141,520, filed Apr. 1, 2015, the contents of each of which are incorporated by reference herein in their entirety.

FIELD

This disclosure generally relates to urinary catheters, and in particular, extended-use, disposable urinary catheters for bladder management.

BACKGROUND

Many people that suffer from bladder issues where they are unable to void and empty the urine in their bladder. One condition that results in this symptom is Neurogenic Bladder. Neurogenic Bladder is often found in people with some form of neurological disorder, such as Stroke, Parkinson's Disease, Alzheimer's, Dementia, Spinal Cord Injury, Multiple Sclerosis, and others. Many of these individuals are required to use intermittent catheters so that urine to exit their bladder. These users may catheterize themselves between 642 times per day. This is often done using Clean Intermittent Catheterization (CIC) as part of an Intermittent Catheterization Program where users will insert catheters at varying intervals throughout the day. This process can be inefficient and has a high risk of Urinary Tract infections, urethral trauma due to False Passage, and other clinical issues. If these individuals were able to decrease the number of times they are catheterized, it would improve the individual's comfort and decrease their risk of infection and other complications. A catheter with a valve that is fully internal to the individual's body, that also allows the user to open and close the valve from outside the body, would minimize the number of times a user has to catheterize themselves and reduce the number of foreign objects entering the urethra. It is, therefore, desirable to provide an extended-use, fully internal, valved catheter, that overcomes, most, if not all, of the preceding problems.

SUMMARY

The present technology relates to systems and method for controlling the urinary voiding process and, in particular, an extended-use device for bladder management.

BRIEF DESCRIPTION OF THE DRAWINGS

The following drawings and the associated descriptions are provided to illustrate the present disclosure and do not limit the scope of the claims.

DETAILED DESCRIPTION

Disclosed herein are embodiments of systems that can be used for bladder management, specifically bladder management for Neurogenic Bladder in a patient. However, the disclosed systems can be used for fluid flow control for other bodily organs as well, and the particular bodily organ described is not limiting. As used herein, the term "user" is intended to include any person trained and able to perform the procedure, including the patient, doctor, caregiver, nurse, etc. The term "patient" and "individual" are intended to be interchangeable. The term "body" used herein is defined as "an animate body" including human, animal, and the like.

Extended-Use Valved Catheter

Figure 1:
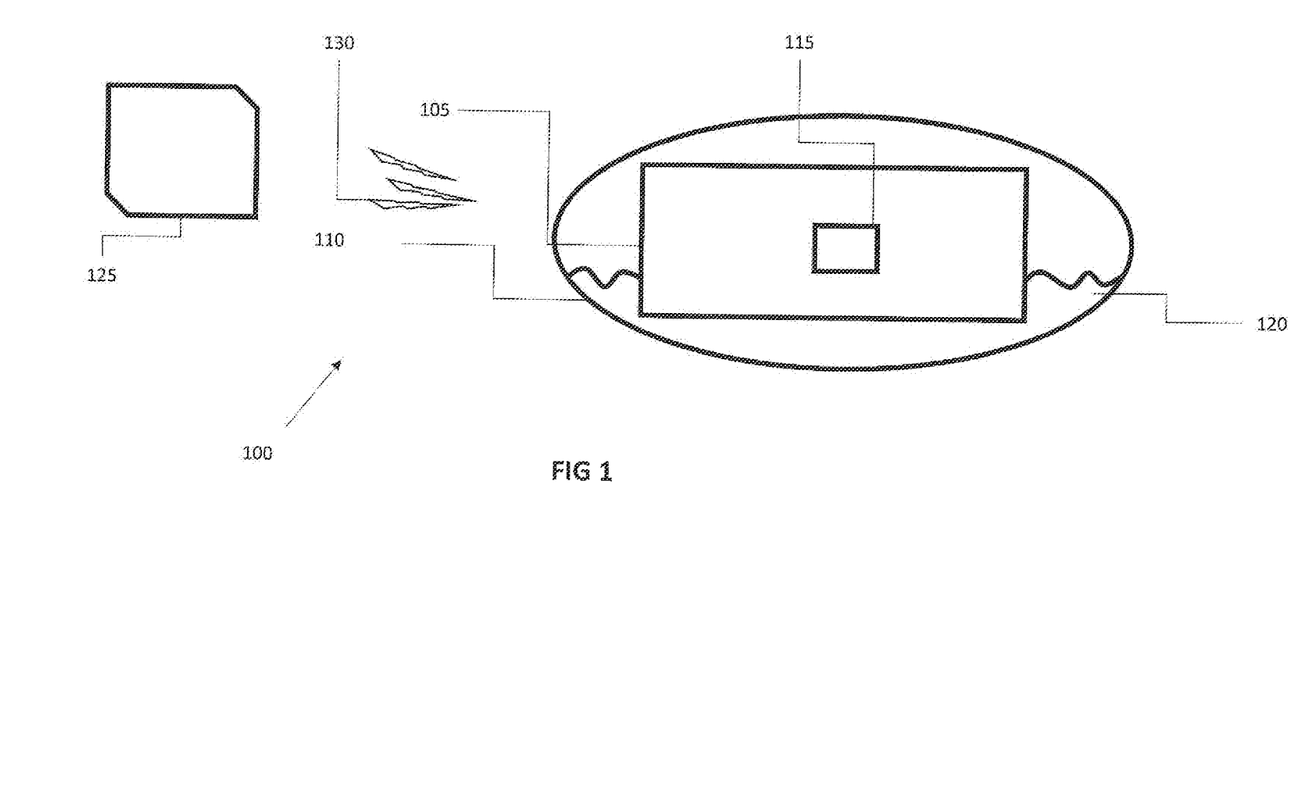
FIG. 1 shows a generalized schematic drawing of a sample extended-use, valved catheter system.

FIG. 1 shows a generalized schematic drawing of a sample extended-use valved catheter system. The bladder management system 100 can comprise a body. The body can be an extended-use catheter 105. The catheter 105 can be shaped and sized to be introduced into the bladder 110 of a patient. The catheter 105 can be fully-internal to the body of the patient such that it is not visible to the naked eye. The catheter 105 can be coated with an antimicrobial coating. The catheter 105 can contain a valve 115 that may control the flow of urine. The valve can be actuated by an external magnet 125 that exerts a magnetic force 130 on the valve to open or close the valve and control fluid flow.

The valve 115 can be configured in such a manner to increase or decrease the flow rate of urine. For example, the valve can have varying degree of valve opening. The valve 115 opening can be configured to dilate and/or expand in order to increase the volumetric flow rate of urine leaving the bladder 110. For example, a pin valve can be used. This valve 115 can also be configured to be actuated by the pressure of urine 120 in the bladder 110. Valve mechanics can be optimized to achieve a reliable level of valve opening at specified pressure levels. Controlling pressure levels inside the bladder can relieve high levels of pressure in the bladder for patients suffering from Neurogenic Bladder. The valve can also be made with inserts that respond to direct force for actuation. The valve may open and allow fluid flow when a user squeezes the valve directly.

Catheter

Figure 2:
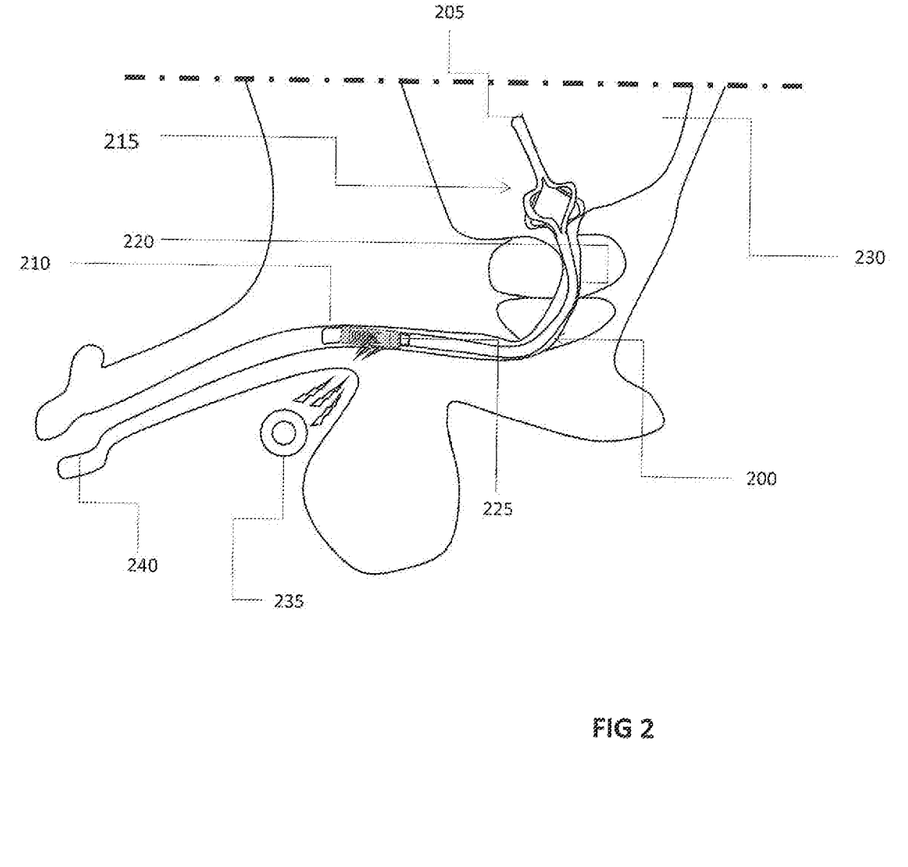
FIG. 2 shows a schematic drawing of the catheter portion of the system in a male urinary control system.

As show in FIG. 2, the catheter 200 can be fully-internal, meaning the catheter 200 is not visible to the naked eye from the exterior, once the catheter 200 is inside the patient's body. The fully-internal catheter 200 can comprise a proximal portion 205 and a distal portion 210. The proximal portion 205 can comprise an anchor 215 that maintains the position of the catheter. The catheter 200 can comprise a lumen 220. The distal portion 210 can comprise a valve 225.

In some embodiments, the urine in the bladder 230 can be voided when the user utilizes a magnet 235 to open the valve 225 and allows the urine to travel through the urethra 240. In some embodiments, the valve 225 can comprise a magnetic ball valve, and the magnet 235 can exert a magnetic force on the valve 225 to cause the valve to open and allow flow of urine. In other embodiments, this magnet 235 can be a combination of electronics that may utilize an electromagnet to open the valve 225. As shown in FIG. 2, a user can place the magnet 235 near the valve 225, e.g. on the skin of patient between the scrotum and the shaft of the penis or underneath the scrotum near the prostate, to open the valve 225. The valve 225 can be closed when the magnet 235 is away from the location of the valve 225 inside the patient's body. For example, the valve 225 can be closed when the actuator is inside a patient's side pocket. This rate of coupling may be optimized to minimize leakage of urine.

Figure 4A:
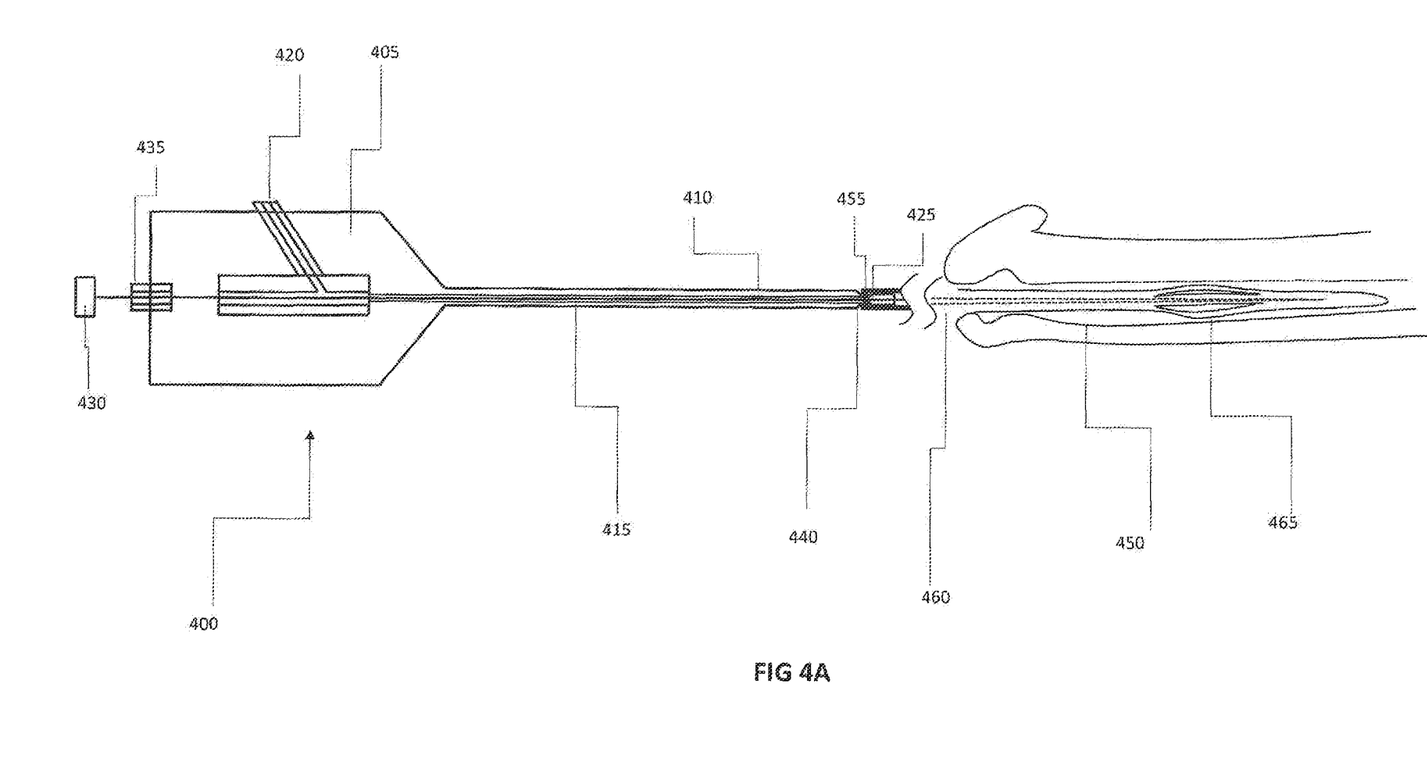
FIG. 4A shows a schematic drawing of an embodiment of an insertion device.

The catheter 200 can be constructed in a shape and of a material that is conducive to entry through the urinary tract utilizing a medical device, such as an insertion device 400 shown in FIG. 4A. For example, the catheter 200 may be constructed of a material similar to other existing intermittent catheters on the market (such as PVC, Latex, Silicone, Polyurethane or any blend of these materials). In some embodiments, once inside the bladder 230, the catheter 200 can comprise an anchor 215 that can fix and/or stabilize the catheter 200 to the wall of the bladder 230.

Valve

Figure 3A:
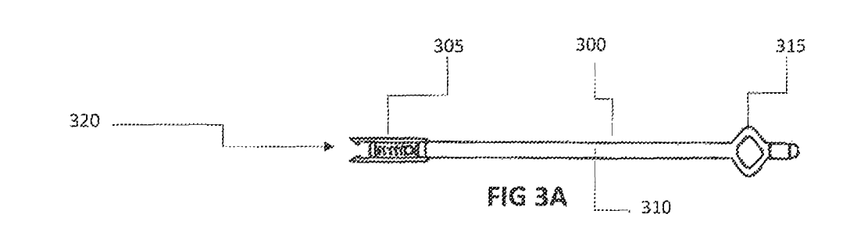
FIG. 3A shows a schematic drawing of an embodiment of the catheter portion of the bladder management system of FIG. 1.
Figure 3B:
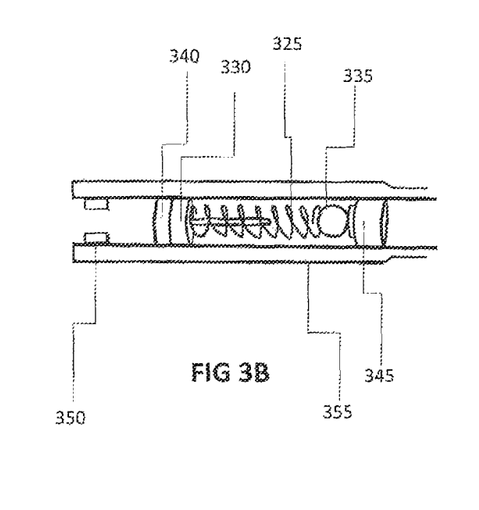
FIG. 3B shows an enlarged view of a valve portion of the catheter of FIG. 3A.

FIGS. 3A to 3O are detailed schematic drawings of the catheter 300 using a ball valve 305. As shown in FIG. 3A, the catheter 300 comprises an elongated midsection 310 between the proximal portion 315 and the distal portion 320. The elongated midsection 3•10 can comprise a flexible tube having a lumen. As shown in FIG. 38, the valve 305 can be a cylindrical magnetic ball valve comprising a spring 325, a spring retainer 330, a ball 335, a distal insert 340, a proximal insert 345, and a mating ledge 350. The proximal portion 315 can comprise a straight tip. In some embodiments, the proximal portion 315 comprises a coude tip.

Figure 3C:
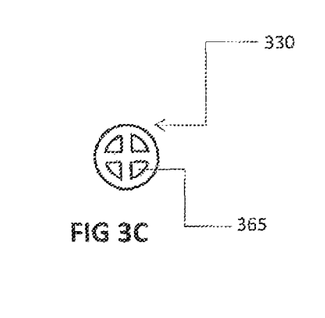
FIG. 3C shows a cross-section view of the valve portion of FIG. 3B across the like a-b.
Figure 3D:
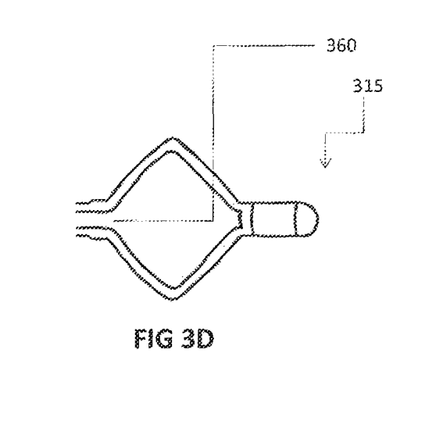
FIG. 3D shows an enlarged view of a anchor of the catheter of FIG. 3A.
Figure 4B:
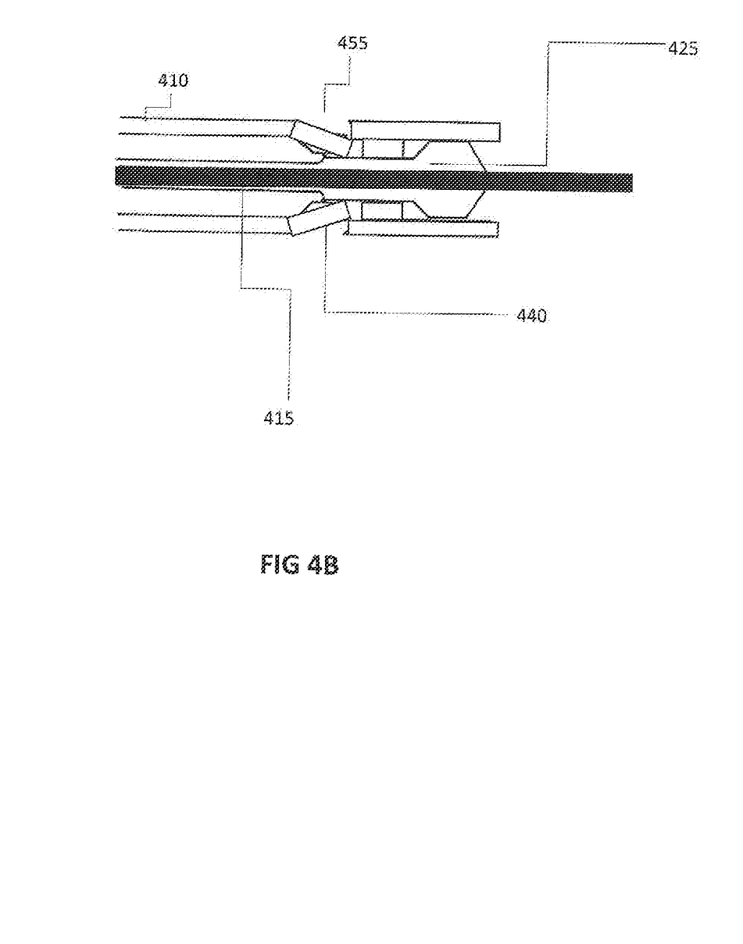
FIG. 4B shows a schematic drawing of an embodiment of the tip of the insertion device of FIG. 4A.
Figure 5A:
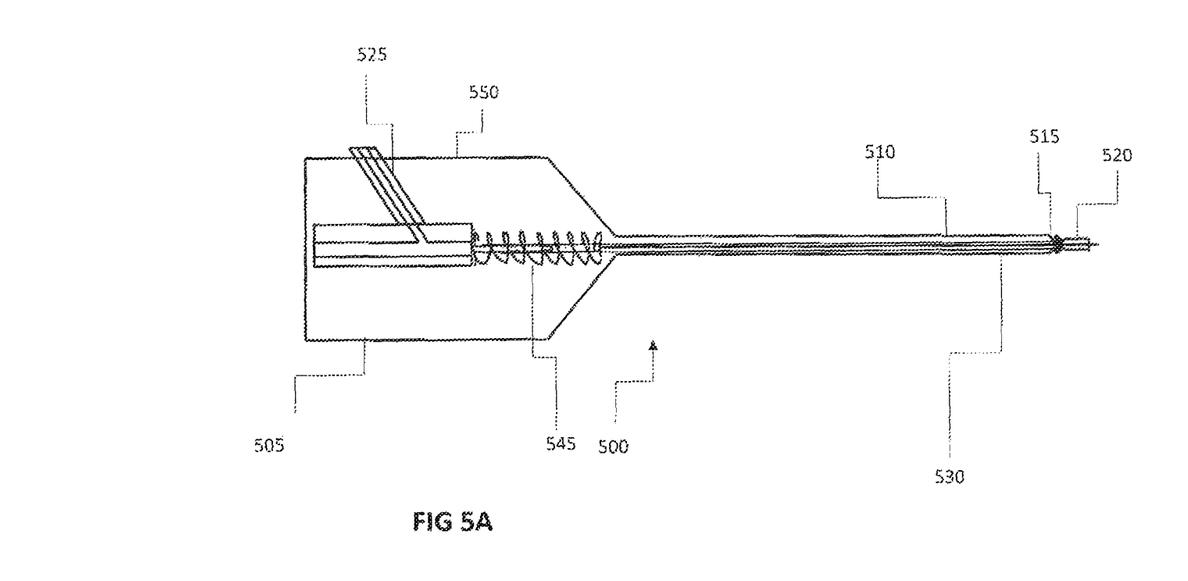
FIG. 5A shows a schematic drawing of an embodiment of an extraction device.

The spring 325 can be coupled to the distal insert 340 and configured to constantly exert tension during opening and closing of the valve 305. The spring retainer 330 can be concentric to the center of the valve 305. The proximal insert 345 can be configured to trap the ball 335 (e.g., by having a ring shape with an inner radius smaller than the radius of the ball 335). The tube 355 can be positioned distal and adjacent to the proximal insert 345. As shown in FIG. 3C, the distal insert 340 and the proximal insert 345 can comprise one or more inlets 365. The inlet 365 can be shaped and sized to pass a pushwire 415 shown and described below in reference to FIGS. 4A and 4B. As shown in FIG. 3D, the proximal portion 315 can comprise a lumen 360 to allow fluid to pass. The mating ledge 350 can comprise a cylindrical insert with a smaller inner diameter than the rest of the valve structure. This difference in diameter allows for the balloon 425 to exert traction on the ledge and translate force during the extraction and insertion processes. The mating ledge 350 can comprise a magnetic material. In some embodiments, the mating ledge 350 can comprise a conductive material that can be used to complete an external circuit and inform a user that the extraction device 500 is mated to the mating ledge 350, as shown in FIG. 5A.

In some embodiments, the valve 305 can comprise a disc, plug, diaphragm, pinch, check, plunger, flap, duckbill, or other valve designed to actuate upon user input and/or at a calculated pressure threshold. In some embodiments, the valve 305 can comprise a manual squeeze valve (not shown) configured to manually open and close. The manual squeeze valve can comprise an elastic body in a closed state without manual adjustment. When the catheter 300 is inside the patient, the user may squeeze the valve 305 from the skin of the patient to open the valve 305. From squeezing the valve 305, the fluid inside the bladder can be drained.

A fully-internal catheter 300 can be used for extended periods and long-term use rather than requiring intermittent replacement as some existing catheter devices require. The long-term use of a fully-internal catheter 300 can aid in patient comfort, prevent and/or reduce psychological trauma from frequent replacement, reduce occurrence of urinary tract infections, etc. The catheter 300 device can be long-term use because it can be inserted and/or removed by utilizing medical devices, e.g., an insertion device 400, an extraction device 500, etc. The removal of the long-term use catheter 300 device can be in a similar manner as when the long-term use catheter 300 device is implanted within the patient. The insertion device 400 and the extraction device 500 can comprise structures corresponding to the mating ledge 350 of the valve 305. The device has been designed in such a way that insertion and extraction can be completed by the user in a rapid and expeditious manner.

As shown in FIG. 4A, the insertion device 400 can comprise a handle 405, an insertion rod 410, a pushwire 415, a Y-Connector 420, a balloon 425, a male luer 430 fitting and a female luer 435 fitting. The pushwire 415 can comprise a mandrel that is made from stainless steel or metal and also may be coated with PTFE or other lubricant to aid in removal. As schematically shown in FIG. 4B, the insertion rod 410 further comprises a mating guide 440 that can be configured to mate with the valve mating ledge 350. For example, as shown in FIG. 48, the mating guide 440 can comprise a tapered insert that mates with the mating ledge 350 of the valve 305.

Figure 4C:
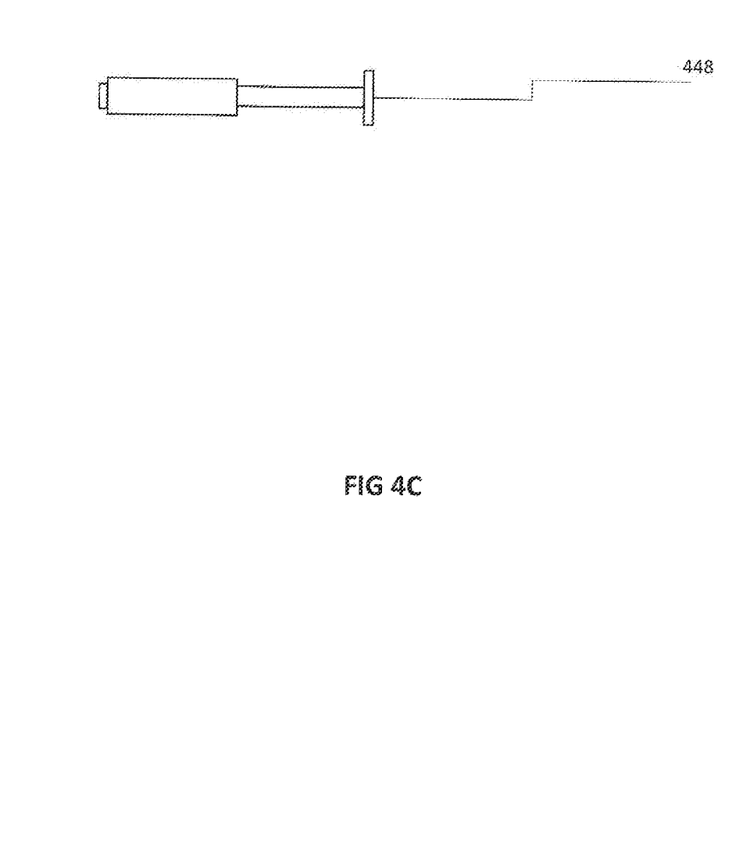
FIG. 4C shows a schematic drawing of an embodiment of a syringe.

To prepare the device for insertion, the user can use the supplied syringe 448 shown in FIG. 4C to inflate the balloon 425. The user will then advance the pushwire 415 until the male luer 430 fitting attached to the pushwire 415 can be secured on the female luer 435 fitting. This will be secured using a standard screw mechanism common of the luer standard.

When prepared for insertion, the insertion device 400 translate force along the axis of travel through the urethra 445 until the user chooses to disengage the mating mechanism 455. This mating mechanism 455 will allow the user to advance the device deeper into the urethra 450 and bladder and also in the opposite direction to allow the user to place the device accurately. This can also allow the user to safely remove the device if for any reason they choose to abort the insertion procedure.

The handle can be in fluid communication with the insertion rod 410. The insertion rod 410 can be configured to allow visual confirmation of material inside of the rod. For example, the rod 410 can comprise a translucent material, such as translucent PVC. The insertion rod 410 can comprise a hollow tube made of a medical grade material, such as nylon. The pushwire 415 can pass through the hollow tube of the insertion rod 410 and the balloon 425 lumen and comprises a shape memory material used in similar medical applications. For example, the pushwire 415 can comprise a Teflon®-coated nitinol or stainless steel wire having a stiffness to allow bending and flexing without causing trauma to the urethra 445 while the catheter 460 is inserted inside the patient's body. The pushwire 415 can have a longitudinal length longer than the combined longitudinal length of the catheter 460 and the insertion rod 410. As shown in FIG. 4A, the pushwire 415 has a length such that a portion of the pushwire 415 extends into the handle 405, while the pushwire 415 extends fully along the erect length of the catheter 460 and the insertion rod 410. During insertion, the tip of the pushwire 415 contacts the catheter 460 tip such that thrusting force from the pushwire 415 transports facilitates the collapse of the anchor 465.

The insertion device 400 and the catheter 460 can be carried in a sterilized pouch. In some embodiments, the insertion device 400 and the catheter 460 can be packaged in a mated state before use. In the mated state, the pushwire 415 extends through the valve 305 such that the valve 305 remains open to allow fluid flow. As shown in FIG. 4A, the anchor 465 can be expanded in the mated state until the user advances the pushwire 415. A user may open the pouch comprising a catheter 460 and the insertion device 400 and insert the catheter 460 into the urethra. The user may advance the catheter 460 by moving the catheter 460 proximally using the insertion device 400. Once the anchor 465 reaches tile bladder, the anchor 465 can expand as the user unscrews the male luer 430 fitting and removes the pushwire 415 to allow the anchor 465 to return to its resting (expanded) state. The fluid within the bladder may drain from an opening 430 of the anchor 465 through the open valve 455, to the insertion rod 410, and eventually to the handle 405. The user may observe presence of fluid inside the insertion rod 410 to visually confirm placement of catheter 460 and that the catheter 460 has successfully reached the bladder. The user can then disengage the male luer 430 fitting and remove the pushwire 415 and allow the anchor 465 to expand. The user can then use the syringe 448 to deflate the balloon 425 and uncouple the insertion device 400 from the catheter 460. The removal of the insertion device 400 can be done subsequent to visual confirmation of the placement of catheter 460. The user can remove the insertion device 400 from the urethra 450 while the catheter 460 remains positioned in the patient's body, In some embodiments, fluid flow through the valve 455 can be prevented before and after the insertion of the catheter 460. For example, the valve 455 can comprise an orifice completely sealed off by the pushwire 415 to prevent fluid flow. In some embodiments, the catheter 460 can comprise a sensor which can notify the user of fluid flow in the catheter 460 upon placing the anchor 465 inside the bladder.

Extraction Device

Figure 5B:
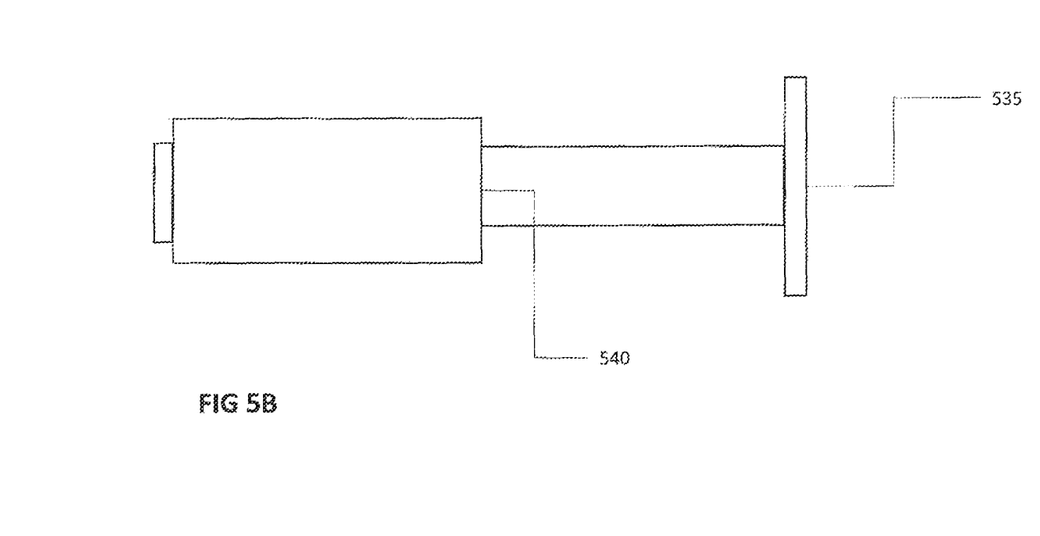
FIG. 5B shows a schematic drawing of an embodiment of a syringe used with an extraction device.

As shown in FIG. 5A, the extraction device 500 can comprise a handle 505, an extraction rod 510, a mating insert 515, a balloon 520, a Y-Connector 525, a pushwire 530, and a spring 545. The extraction device 500 can further comprise a syringe 535 and a syringe lock 540 as shown in FIG. 5B. The extraction rod 510 can comprise a tube with the mating insert 515 attached at one end. The extraction device 500 can comprise a balloon 520 that is connected by a tube 630 to the Y Connector 525. In some embodiments, this balloon 520 can also be bonded to the pushwire 530 and Y Connector 525 such that the advance of the balloon 520 is equal to the advance of the pushwire 530 and Y Connector 525 inside the extraction rod 510. The balloon 520 can be configured to mate with the mating ledge 350 of the valve 305. For example, the balloon 520 can be advanced beyond the mating ledge 350 in its deflated state, then inflated with the syringe 535 to expand and catch the mating ledge 350. This mating ledge 350 can be sized such that it will provide resistance for the inflated balloon 520 to exert the force required to collapse the anchor 465 and extract the entire device.

The handle 505 can comprise an ergonomic structure and can house a spring 545. The Y Connector 525 can be exposed such that the user can advance and rotate the Y connector 525 to lock it in place, preventing it from retraction. This locking shape 550 allows the balloon 520 to remain in the advanced position which positions the balloon 520 beyond the mating ledge 350 in the optimal position for inflation and extraction. The user can then inflate the balloon 520 by using the syringe 535 and locking the Y-Connector 525 in the position where the balloon 520 will remain inflated inside the valve 305.

The extraction rod 510 of the extraction device 500 can be inserted in the urethra 450 of a patient wearing the fully-internal catheter 460. The user can determine connection of the mating insert 525 to the valve mating structure 350 by noticing when the extraction device 500 encounters resistance. Prior to inserting the extraction device 500 the user should physically take stock of where the valve 305 is located by identifying this location visually and physically. The valve 305 ending can be located through tactile sensation due to the enlarged nature of the urethra. They can also apply traction to hold the valve 305 in place to assist in the connecting of these two devices. In some embodiments, magnetic or conductive material can be emplaced in the valve mating ledge 350 and the mating insert 515 of the extraction tool 500 to provide tactile, visual or auditory feedback for the user to know when the two devices are properly mated.

When the two parts are properly mated the user may advance and rotate the Y Connector 525 to lock it in place. This advances the balloon 520 beyond the mating ledge 350 positioning it for proper inflation. Once inflated and both the Y Connector 525 and Syringe 535 are locked in place, the user may move the extraction device 500 to extract the catheter 300 out of the patient's body and dispose the entire assembly.

In the event that the user is unable to successfully connect the extraction tool 500 and the mating ledge 350, the extraction device 500 can be removed from the urethra and reset from the locking position to the unlocked position with the balloon 520 deflated. The user can then repeat the extraction procedure to attempt another removal of the catheter 300.

In some embodiments, the extraction tool 500 may be packaged in a semi-rigid sterile container to ensure safe transport of the extraction tool 500 over extended periods of time. This may comprise a combination of rigid and semi-rigid packaging materials (including cardboard, plastics, and metal parts) to ensure that the device stays securely in the sterile pouch despite potentially rugged transport with the user over the length of the service life for the catheter 300.

Among the many advantages of this invention include increasing the quality of life for individuals suffering from neurogenic bladder by: 1. reducing the risk of medical issues (urinary tract infections, false passage, etc.); 2. eliminating the need for indwelling or intermittent catheters and decreasing the number of catheters required for daily use (because of increased accuracy with which the user knows when catheterization is required); 3. allowing the user to control bladder voiding; 4. accommodating implanted, semi-permanent (useful life 3-6 months) device via minimally invasive means (via catheter): and 5. minimizing problems from incontinence and related psychological impact (emotional trauma from accidental urinary voiding).

Although embodiments of the invention have been, shown and described, it is to be understood that various modifications, substitutions, rearrangements and different parts, components, equipment, elements and/or process (method) steps, as well as other uses, of the wireless pressure sensor and valve for bladder can be made by those skilled in the art without departing from the novel sprit and scope of this invention.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

As used in any embodiment herein, the term "module" may refer to software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The modules may, collectively or individually, be embodied as circuitry that forms part of a larger system, for example, an integrated circuit (IC), system on-chip (SoC), desktop computers, laptop computers, tablet computers, servers, smart phones, etc.

Any of the operations described herein may be implemented in a system that includes one or more storage mediums having stored thereon, individually or in combination, instructions that when executed by one or more processors perform the methods. Here, the processor may include, for example, a server CPU, a mobile device CPU, and/or other programmable circuitry.

Unless otherwise indicated, all numbers expressing quantities of ingredients, properties such as molecular weight, reaction conditions, and so forth used in the specification and claims are to be understood as being modified in all instances by the term "about". Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported, significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A bladder management system comprising:
 a fully-internal catheter configured to be placed inside of and retained in a bladder of a patient's body and invisible to human eyes from outside of the body once inside the bladder, the fully-internal catheter comprising (a) a lumen extending through the catheter, wherein the lumen is configured to transport fluid, a proximal end and a distal end, wherein the distal end comprises an opening that is in communication with the lumen, (b) a retaining portion having a first configuration in which it can pass through the urethra, and a second, expanded configuration in which it is configured to be retained in the bladder and cannot pass through the urethra, the retaining portion juxtaposed the proximal end, and (c) an electromagnetic valve that has a first, open position and a second, closed position, and (d) a mating ledge juxtaposed the distal end and being between the electromagnetic valve and the distal end; and an insertion device comprising a mating guide configured to mate with the mating ledge, wherein the mating guide has a first configuration in which it does not mate with the mating ledge, and a second, expanded configuration in which it does mate with the mating ledge.

2. The system of claim 1, wherein the mating guide further comprises a tapered insert.

3. The system of claim 1, wherein the mating guide comprises a balloon.

4. The system of claim 1, wherein the mating guide comprises a balloon catheter and a Y-Connector configured for inflation of the balloon catheter to the second, expanded configuration and deflation of the balloon catheter to the first configuration.

5. The system of claim 1 that further comprises an extraction device having a mating guide with a first configuration in which it does not mate with the mating ledge, and a second, expanded configuration in which it does mate with the mating ledge.

6. The system of claim 1, wherein the insertion device mating guide can be selectively locked in the second, expanded configuration to facilitate insertion of the catheter.

7. The system of claim 1, wherein the mating guide comprises a Y-Connector attached to a balloon catheter.

8. The system of claim 7 that further includes a magnet configured to open and close the electromagnetic valve.

* * * * *